(12) United States Patent
Deves et al.

(10) Patent No.: US 6,551,832 B1
(45) Date of Patent: *Apr. 22, 2003

(54) AUTOMATIC MULTI-REACTOR CATALYST EVALUATION METHOD AND DEVICE WITH A HEAVY FEEDSTOCK

(75) Inventors: Jean-Marie Deves, Vernouillet (FR); Jean-Yves Bernhard, Mennecy (FR); Bernard Chatelain, Jouy le Moutier (FR); Pierre Toutant, Franconville-la Garrenne (FR); José Brandely, Savigny sur Orge (FR); Corinne Guitton, Chatou (FR)

(73) Assignee: Institut Francais du Petrole, Cedex (FR)

( * ) Notice: Subject to any disclaimer, the term of this patent is extended or adjusted under 35 U.S.C. 154(b) by 356 days.

This patent is subject to a terminal disclaimer.

(21) Appl. No.: 09/604,731

(22) Filed: Jun. 28, 2000

(30) Foreign Application Priority Data

Jun. 28, 1999 (FR) .............................. 99 08282

(51) Int. Cl.$^7$ .............................................. G01N 31/10
(52) U.S. Cl. ................... 436/37; 436/147; 436/159; 436/161; 436/164; 436/172; 436/173; 422/62; 422/93; 422/104; 422/196; 422/197
(58) Field of Search ................... 436/37, 147, 159, 436/161, 164, 172, 173; 422/62, 93, 104, 196, 197

(56) References Cited

U.S. PATENT DOCUMENTS

| | | | |
|---|---|---|---|
| 3,431,077 A | * 3/1969 | Danforth | 436/37 X |
| 4,099,923 A | 7/1978 | Milberger | |
| 5,266,270 A | 11/1993 | Ajot | |
| 5,356,756 A | * 10/1994 | Cavicchi et al. | 430/315 |
| 6,063,633 A | * 5/2000 | Willson, III | 436/37 |

FOREIGN PATENT DOCUMENTS

JP  61-292054  12/1986

OTHER PUBLICATIONS

L. Kiezel et al, Chemia Stosowana 1968, 12, 407–415.*
N. V. kul'kova et al, Khim. Prom. 1968, 44, 656–658.*
J. J. Hanak J. Mater. Sci. 1970, 5, 964–971.*
J. V. Jensen et al, in "Proc. Int. Congr. Catal. 6th" vol. 2, G. C. Bond et al, ed. 1977, Chemical Society, 796–805.*
R. Wenske Tech. Umweltschutz 1976, 14, 169–197.*
C. E. Berkoff et al, Chem. Ind. 1981, 68–69.*
V. I. Spitsyn et al, Kinet. Katal. 1982, 23, 759–761.*

* cited by examiner

Primary Examiner—Arlen Soderquist
(74) Attorney, Agent, or Firm—Antonelli, Terry, Stout & Kraus LLP

(57) ABSTRACT

A method and to an equipment carry out measurements on an effluent resulting from a chemical reaction taking place in a reactor containing a catalyst. The method includes, in combination, injecting at least one feedstock into each of at least two reactors, separating the gas and liquid phases downstream from each reactor, sending the separated gas phase to be measured and analyzed while the other gas phases coming from the other separators are discharged, sending the separated liquid phase to be analyzed and measured, and automatically monitoring and controlling the chemical reaction in the reactors, the analysis and measurement cycle performed on the gas phase and the analysis and measurement cycle performed on the liquid phase.

10 Claims, 5 Drawing Sheets

AUTOMATIC MULTI-REACTOR CATALYST EVALUATION METHOD AND DEVICE WITH A HEAVY FEEDSTOCK

FIELD OF THE INVENTION

The present invention relates to an automatic equipment intended for multi-reactor testing of chemical reactions, possibly in the presence of a catalyst. This equipment working under high pressure and high temperature conditions allows to use as the reagent heavy hydrocarbon cuts obtained from vacuum distillation of crude oil. This equipment comprises an elaborate automation system allowing fast and simultaneous evaluation of several sets of operating conditions. Acquisition of data on the progress of the reaction and on the performances of solid catalysts is thus possible.

The reaction products are separated at the outlet of the reactors into two phases (gas and liquid). The gas fractions are analyzed in line by chromatography, the liquid fractions are analyzed by simulated distillation. The performances are determined by automatic drawing up of a material balance. The elaborate automation of the assembly allows to carry out simultaneous cycles of all the reactors without the operator's intervention.

BACKGROUND OF THE INVENTION

The development of industrial refining and petrochemistry processes requires acquisition of data on the chemical reactions that take place. When these reactions are catalyzed, research and development of the catalysts required involve evaluation of the performances thereof. In the laboratory, these data acquisitions and evaluations are performed in pilot plants which reproduce on a small scale the industrial operating conditions.

There are many types of equipments allowing to measure the rate of progress of chemical reactions or the activity of solid catalysts. In the field of petroleum refining and of petrochemistry, the operating conditions under which these measurements are performed are as follows:

pressure ranging between $1.10^5$ and $3.10^7$ Pa, temperature ranging between ambient temperature and 800° C., liquid and/or gaseous reagent flow rates expressed in form of hourly volume flow rate per unit of volume of reactor or catalyst (hourly space velocity) ranging between 0.01 and 100 $h^{-1}$ and by the ratio of the molar flow rate of gas (most often hydrogen) and the liquid reactive hydrocarbon ($H_2$/HC) ranging between 0.01 and 50.

More precise selection of the operating conditions depends on the type of process or of catalyst considered. It can be, for example, one of the following industrial applications: reforming, isomerization, hydrocracking, hydrotreating, selective hydrogenation, conversion of aromatics or oxidation.

Solid catalysts are used as balls, extrudates or powder of variable grain size. The quantities of catalysts used in these pilot plants generally range between some grams and several ten or hundred grams. These quantities are relatively great and they can be a limitation to the use of these pilot plants. In particular, during research or development of a new catalyst, the quantities of solid catalyst available for testing are quite often limited (less than one gram) and there can be a great number of catalytic solid variants. All the available samples are therefore not necessarily tested.

The most isothermal operating conditions possible are sought for the reactors. This is generally obtained by placing the reactor in an oven consisting of several zones whose temperature is independently controlled (document U.S. Pat. No. 5,770,154). The dimensions of these reactors also receive particular attention. In particular, the length/diameter ratio of the catalyst bed is most often selected between 50 and 200 so as to ensure proper flow of the reagents and of the products through the catalyst, failing which diffusion or backmixing limiting phenomena disturb measurement of the progress rates and performances of the catalyst.

Catalysts generally require, prior to the reaction stage proper, an activation stage which changes one or more of their constituents into a really active element for catalysis. It may be an oxide reduction in hydrogen in the case of supported metal catalysts or sulfurization in the presence of a sulfur-containing forerunner for catalysts based on metal sulfides. In conventional pilot plants with large dead volumes and a great thermal inertia because of the size of the ovens, this activation stage is generally long (typically of the order of several hours to several ten hours).

The nature of the reagent used (most often a hydrocarbon or a mixture of hydrocarbons) depends on the application considered. It can be a pure hydrocarbon such as, for example, normal hexane, normal heptane or cyclohexane, or more or less heavy or more or less wide petroleum cuts such as, for example, gasolines, gas oils or distillates from crude oil distillation. The quantities of reagent consumed depend of course on the size of the reactor and on the operational time. Most often, however, the performances are calculated from inlet-outlet material balances performed over relatively long periods (some hours to several ten hours). These periods are necessary to allow to collect a sufficient amount (several liters to several ten liters) of products in order to draw up a precise material balance. Using a pure hydrocarbon-containing molecule whose manufacturing cost is high is not always possible under such conditions.

Furthermore, during the period of evaluation of the material balance, which can be long, the catalyst may undergo a certain deactivation. Since the activity of the catalyst is not the same between the beginning and the end of the material balance, the performances calculated in fine only reflect an average behaviour of the catalyst, far from the real evolution of the performances in time.

The effluents coming from the reactor are conventionally separated by expansion and cooling into two phases: liquid and gaseous, whose characteristics and compositions are analyzed separately. These separate separation and analysis operations inevitably lead to product losses which reduce the accuracy of the global material balance. In some cases, analysis of all of the products cannot be carried out at one go with a single chromatographic analyzer. It is then possible to perform an in-line analysis before liquid/gas separation together with an analysis of the gaseous fraction taken after separation. This allows to draw up accurate material balances in this case (document U.S. Pat. No. 5,266,270).

Automation of conventional pilot plants remains quite often underdeveloped. The size of these plants and observance of the safety regulations linked with automatic operation make this automation complex and expensive. In particular, the operating conditions determining the severity with which the reaction progresses (temperature or volume flow rate of the reagent) are most often manually adjusted by the plant operator.

To sum up, the conventional pilot plants commonly used for measuring the progress of chemical reactions and the performances of catalysts have a certain number of drawbacks, such as:

the necessity for a large quantity of catalyst and of reagent, the length of the set-up time and the time required for drawing up the material balance required to determine the performances, the performances reflect an average behaviour of the catalyst over a relatively long period, the performance measurement frequency is relatively low, complete operation automation is difficult and expensive.

On account of these drawbacks, conventional pilot plants are not very well suited for fast and precise screening, among many catalytic solids, of the most interesting solids for development of a new catalyst or study of a new reaction.

SUMMARY OF THE INVENTION

The present invention thus relates to an equipment for performing measurements on an effluent resulting from a chemical reaction taking place in a reactor containing a catalyst. It comprises in combination:

at least two reactors, means for injecting at least one feedstock into each reactor, means for separating the gas and liquid phases downstream from each reactor, distribution means for sending the gas phase coming from the separation means to first analysis and measuring means while the other gas phases coming from the other separators are discharged, second analysis and measuring means intended for the liquid phase coming from the separation means, means intended for automatic monitoring and control of the chemical reaction in said reactors, of the cycle of analysis and measurement performed on the gas phase and of the cycle of analysis and measurement performed on the liquid phase.

The distribution means can comprise at least two inlet ways and two outlet ways, at least one closed-loop line divided in four sections by four controlled sealing elements; each one of said four ways can communicate with a single section so that the inlet ways are connected to two opposite sections and the outlet ways are connected to the other two sections.

The equipment can comprise four reactors.

The distribution means can comprise two closed-loop lines and the outlet ways can communicate with each other two by two so as to form a distribution device with four inlet ways and two outlet ways.

The inside diameter of the reactors can range between 0.5 and 3 cm, preferably between 1 and 2 cm, their length can range between 10 and 50 cm, preferably between 15 and 25 cm.

The present invention also relates to a method intended for analysis and measurement on an effluent produced by a chemical reaction taking place in a reactor containing a catalyst, wherein the following stages are carried out:

there are at least two reactors, at least one feedstock is injected into each reactor, the effluent produced by each reactor is separated into a liquid phase and a gas phase, the gas phase is alternately sent to measuring and analysis means by distribution means, analyses and measurements are carried out on the liquid phase, the progress of the reaction, analysis and measurement cycles is controlled for each phase with the aid of automatic monitoring and control means.

The material balances of each reaction can be determined.

The temperature and the pressure of the gaseous effluents can be controlled between the outlet of the separation means and the measuring and analysis means, including the distribution means, so that said effluent remains gaseous.

The method and the equipment according to the invention can be advantageously applied for comparing the characteristics of different catalysts used in each reactor and/or for determining the optimum conditions of use of a catalyst for a determined reaction by varying the reaction parameters in each reactor.

The object of the equipment according to the invention is thus multiple. It notably allows:

automatic measurement of the progress of chemical reactions and of catalytic performances in parallel in several reactors, use of small quantities of catalyst compatible with fast selection from a great number of samples, isothermal use of the catalyst in the reactors, automatic and in-line analysis of the gaseous reaction products of each reactor and simulated distillation analysis of the liquid fractions collected, selective and frequent measurement of the reaction and catalytic performances, complete progress of the operating cycles without the operator's intervention.

BRIEF DESCRIPTION OF THE DRAWINGS

Other features and advantages of the present invention will be clear from reading the description hereafter, given by way of non limitative example, with reference to the accompanying figures wherein.

DETAILED DESCRIPTION

Figure 1:
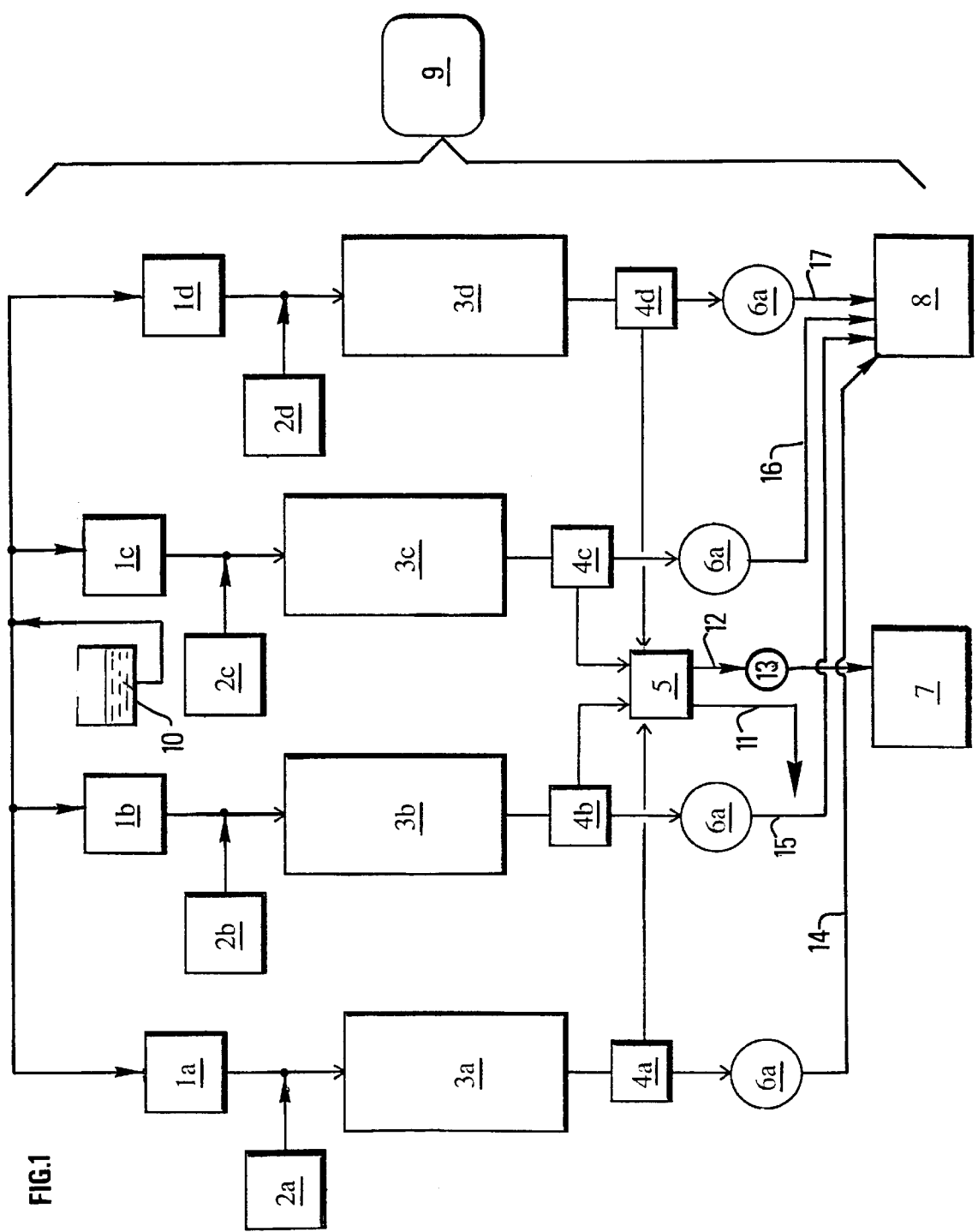
FIG. 1 is the flowsheet of a device according to the invention.

The equipment according to the invention, for which a flowsheet example for four reaction assemblies (suffix a, b, c and d) is given in FIG. 1, consists of the following various subassemblies:

a system for injecting gaseous (2a to 2d) and liquid (1a to 1d) reagents, connected to each reactor 3a, 3b, 3c and 3d, a reaction section (3a to 3d) comprising several microreactors and a heating system, a liquid/gas separation system (4a to 4d) at the outlet of each reactor, means (5) intended for distribution of the gaseous effluents coming from the reactors, an analysis system (7) with in-line extraction of the sample to be analyzed, a system for collecting the liquid product samples (6a to 6d), a system (8) for analysing the liquid products by simulated distillation, a monitoring/control unit (9) managing the assembly.

Each gaseous reagent injection system (2a to 2d) consists of a pressure reducer-regulator, a safety valve, a pressure detector and a mass flow rate regulator. The gaseous reagent is most often hydrogen. The pressure reducer-regulator allows to maintain a constant pressure at the reactor inlet (ranging between 0 and $1.8 \cdot 10^7$ Pa in relative value) from the available supply pressure. The flow rate range provided by the mass flow rate regulator ranges from 5 to 500 l/h with a 1% relative precision. These regulators can be, for example, models 5850E marketed by BROOKS.

The liquid reagent is injected into each reactor by means of a pump (1a to 1d) that can be a piston type pump with a total volume of at least 500 cm$^3$ such as, for example, the 500D pumps marketed by ISCO. This type of pump allows high-pressure and high-precision injection, without surges, of very small quantities of liquid (ranging between 0.05 and 100 cm$^3$/h). If the viscosity at ambient temperature of the reagent is not sufficient to allow correct injection, this pump must be equipped with a system allowing to heat it to a moderate temperature (50 to 120° C.). Similarly, the supply vessel 10 of pump 1a (or 1b, 1c, 1d) and the reagent circulation lines between supply vessel 10, the pump and the reactor must be heated for liquid reagents whose viscosity is not sufficient at ambient temperature. Mixing of the liquid and gaseous reagents is performed upstream from the reactor.

In cases where activation of the catalyst requires the presence of a particular chemical compound, it is possible to feed the liquid reagent injection pump from another supply vessel containing this compound dissolved in a solvent.

The inside diameter of the reactors used or microreactors ranges between 0.5 and 3 cm, preferably between 1 and 2 cm for a length ranging between 10 and 50 cm, preferably between 15 and 25 cm. They are arranged vertically in an oven. The direction of flow of the reagents can be ascending or descending. These reactors are made of heat-resisting steel (of Inconel 625 type for example). The cylindrical catalyst bed is located in the central part thereof, it contains between 0.1 and 10 g catalyst. This bed is preceded by a bed of inert material (silicon carbide for example) having the same grain size as the catalyst, whose purpose is to provide preheating and vaporization of the reagents. These reactors are axially equipped with small-diameter thermocouples (0.5 mm for example) allowing to measure the temperature at different points along the longitudinal axis. The heating oven of these reactors consists of at least two (preferably four) zones that are independent as regards temperature control. The first zone corresponds to the reagent preheating and vaporization zone, the second one to the catalyst bed. The presence of various individually controlled zones guarantees isothermal operation of the reactor along the longitudinal axis thereof The system (4a to 4d) located at the outlet of each reactor consists of two successive liquid/gas separation cells. A pressure-reducing valve for expansion to atmospheric pressure is installed on the gas fraction outlet line. This valve can be, for example, a dome type overflow valve marketed by TESCOM. In order to provide total separation between the liquid and gas fractions, the lower part of the first separation cell is maintained at an average temperature (between 30 and 60° C.), whereas the upper part of this cell is cooled to between 0 and 25° C. The second cell is at ambient temperature.

Distribution means (5) comprise a series of valves allowing one of the gaseous streams coming from separators 4a, 4b, 4c, 4d to be sent to analyzer (7) or to be discharged, respectively through lines 12 and 11. At a given time, only one outlet way of separators 4 is communicated with the way leading to the analyzer, the other ways being communicated with the discharge channel. A positive-displacement meter 13 intended for the gaseous stream is installed on the way leading to the analyzer.

An example of distribution means 5 is illustrated in FIGS. 4a, 4b, 4c and 4d.

Figure 4A:
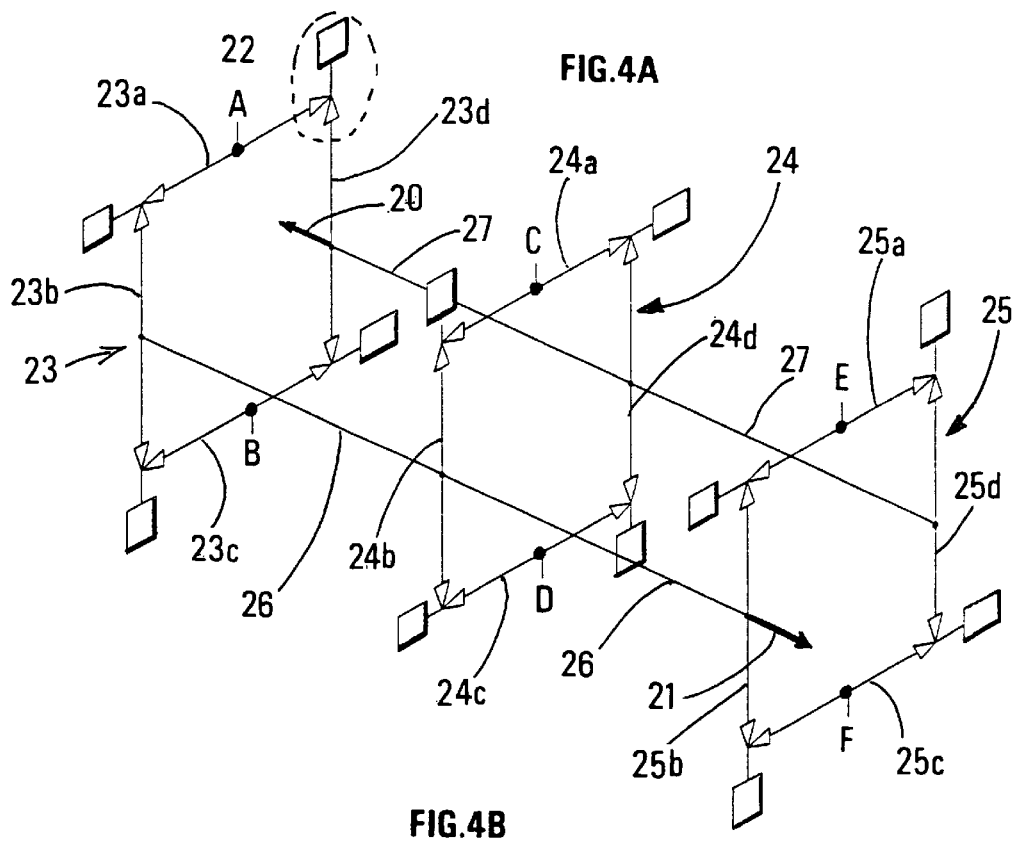
FIGS. 4a, 4b, 4c and 4d show the principle of a selection valve of the equipment according to the invention.

FIG. 4a shows the principle of the selection valve, which can have 2, 4, 6, . . . , 2n inlet ways and two outlet ways. The two outlet ways bear reference numbers 20 and 21. In the case shown here, i.e. with 6 inlet ways, the latter are designated by A, B, C, D, E and F. Reference number 22 designates a line sealing element, for example a needle cooperating with a conical seat, activated by a pneumatic or hydraulic piston type operator. The design of the present valve is based on one or more closed-loop lines (23, 24, 25). Each loop is divided into four line sections 23a, 23b, 23c, 23d; 24a, 24b, 24c, 24d; 25a, 25b, 25c, 25d. Each section is delimited by a sealing element 22. Each loop 23, 24 or 25 comprises two lines for two inlet ways A, B or C, D or E, F. These two inlet lines open each onto two opposite sections, 23a, 23c; 24a, 24c; 25a, 25c. The other two sections communicate each directly with one of the two outlet ways 20, 21.

Thus, if we consider the simplest case of such a valve with a single loop (two inlet ways), controlling one or the other of sealing elements (22) delimiting an inlet line allows to select communication of this inlet with one of these two outlets or the other.

If the measuring equipment comprises more than two reactors, the selection valve comprises at least two loops whose outlet lines are connected together, for example by lines 26, 27 as shown in FIG. 4a.

A selection valve of this type allows to use sealing elements 22, for example marketed by NOVA SWISS, which can withstand both high pressures and high temperatures, as it is the case downstream from the reactors.

Furthermore, the configuration of the lines can be such that it constitutes a minimum dead volume, which is essential for the quality of the measurements and of the comparisons between the reaction cycles.

Figure 4B:
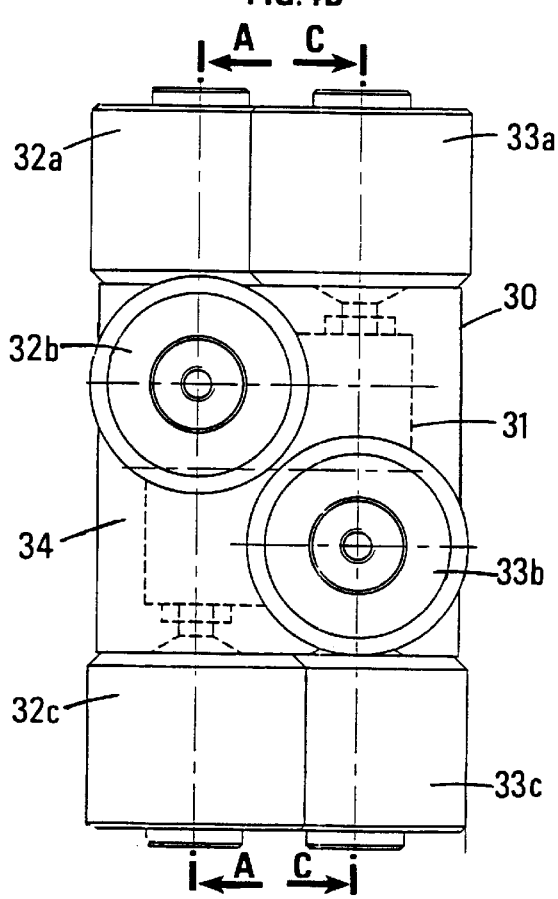

FIG. 4b shows, in side view, a selection valve comprising a housing 30 containing a block 31 wherein the effluent passage lines have been pierced. Reference numbers 32a, b, c and d (FIG. 4c) designate the pneumatic operators which actuate the sealing elements of the various line sections. Space 34 is filled with a thermal insulating material. FIG. 4b shows a valve with two loops, i.e. according to the description above, with four inlet ways (for reactors 3a, 3b, 3c and 3d) and two outlet ways. The staggered arrangement of the pneumatic operators allows to have a minimum distance between the two planes containing the two loops. The length of internal lines (26, 27 notably) is thus reduced, which decreases the dead volumes.

Figure 4C:
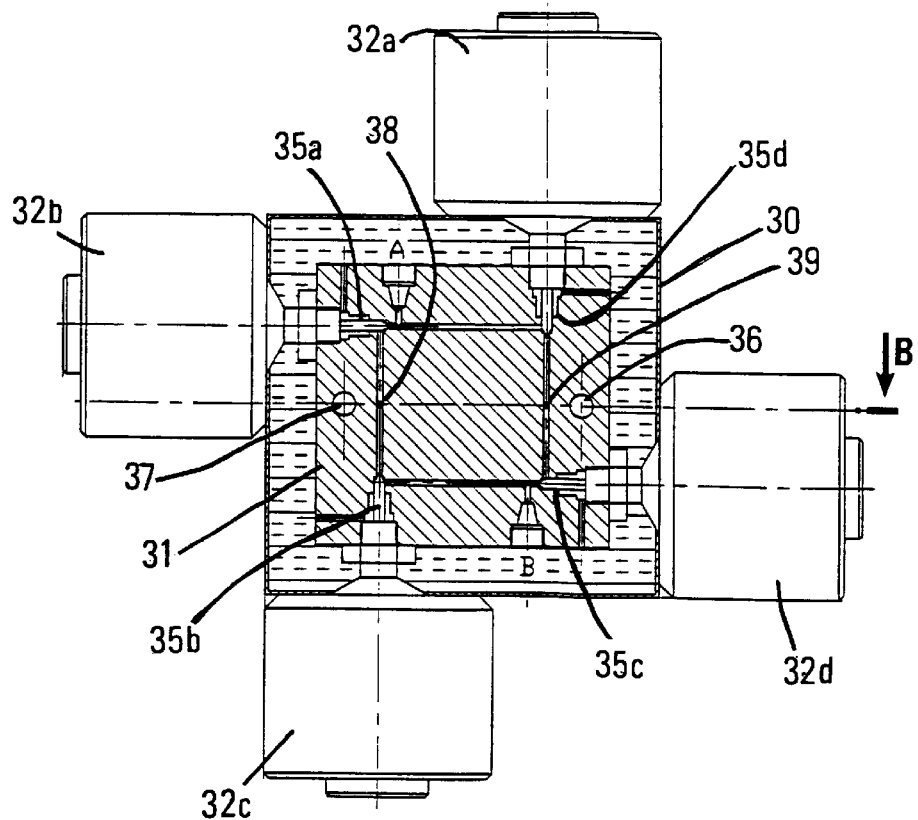

FIG. 4c is a cross-section along plane AA (FIG. 4b). The four line sections are made by means of four non-through bores provided in block 31. Inlet ports (35a, b, c, d) are machined so as to receive the needle of the sealing element and the joint stuffing-box type packings. In order to withstand average temperatures of about 250° C., the packings can be made of PEEK (polyetheretherketone).

Bores 36 and 37 in block 31 are used for heating and/or regulating elements.

Reference numbers 38 and 39 show the lines connecting the loop sections to the two outlets of the selection valve.

Figure 4D:
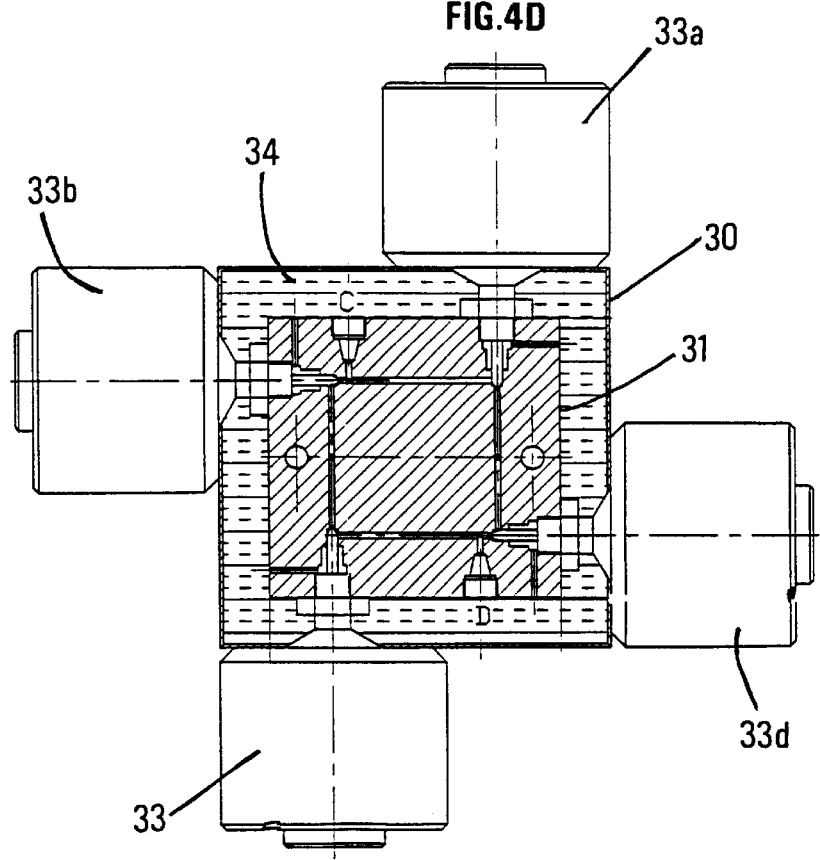

FIG. 4d is a view of section CC in the plane containing the second line loop. The structure is identical to that of the first loop illustrated by FIG. 4c, but the sealing elements are arranged in another direction (at 90°) so that operators 33a, b, c, d are arranged in staggered rows in relation to operators 32a, b, c, d.

Analyzer (7) allows detailed analysis of the gaseous products resulting from the chemical reaction. This analyzer is equipped with a valve, for example marketed by VALCO, for taking samples of these products. The analyzer can be a gas phase chromatograph, i.e. equipped with one or more chromatographic columns, capillary or not, separating the reaction products by retention time difference and with flame ionization detectors. This analyzer can be, for example, a 5890 model marketed by HEWLETT PACKARD, or GC2000 marketed by THERMO QUEST. The capillary column can be, for example, an apolar 50-m long and 0.2-mm diameter PONA type column.

At the outlet of separation systems (4a to 4d), the liquid product fractions are collected in several bottles (1 to 5 cm$^3$ in volume) in barrel-type arrangement at the outlet of a selection valve. This system (6a to 6d) allows to measure, by weighing the bottles, the quantity of liquid collected during a given operating period and direct analysis of these liquid fractions by analyzer (7). This analyzer is a gas phase chromatograph equipped with an automatic sampler to which the collection bottles are fitted and with an assembly allowing to perform simulated distillations. This function is shown by connections 14, 15, 16 and 17 between liquid fraction collection means 6a, 6b, 6c, 6d.

The material balance required for performance calculation is made from analyses of the liquid and gas fractions and from measurement of the volume of gas and of the weight of liquid collected over a given period.

Control system (9) manages all the various temperature, pressure, flow rate regulations, valves and actuators. This system is built around a SIEMENS automaton S7-400 and a FIX-DEMACS control software marketed by Intellution.

Figure 2:
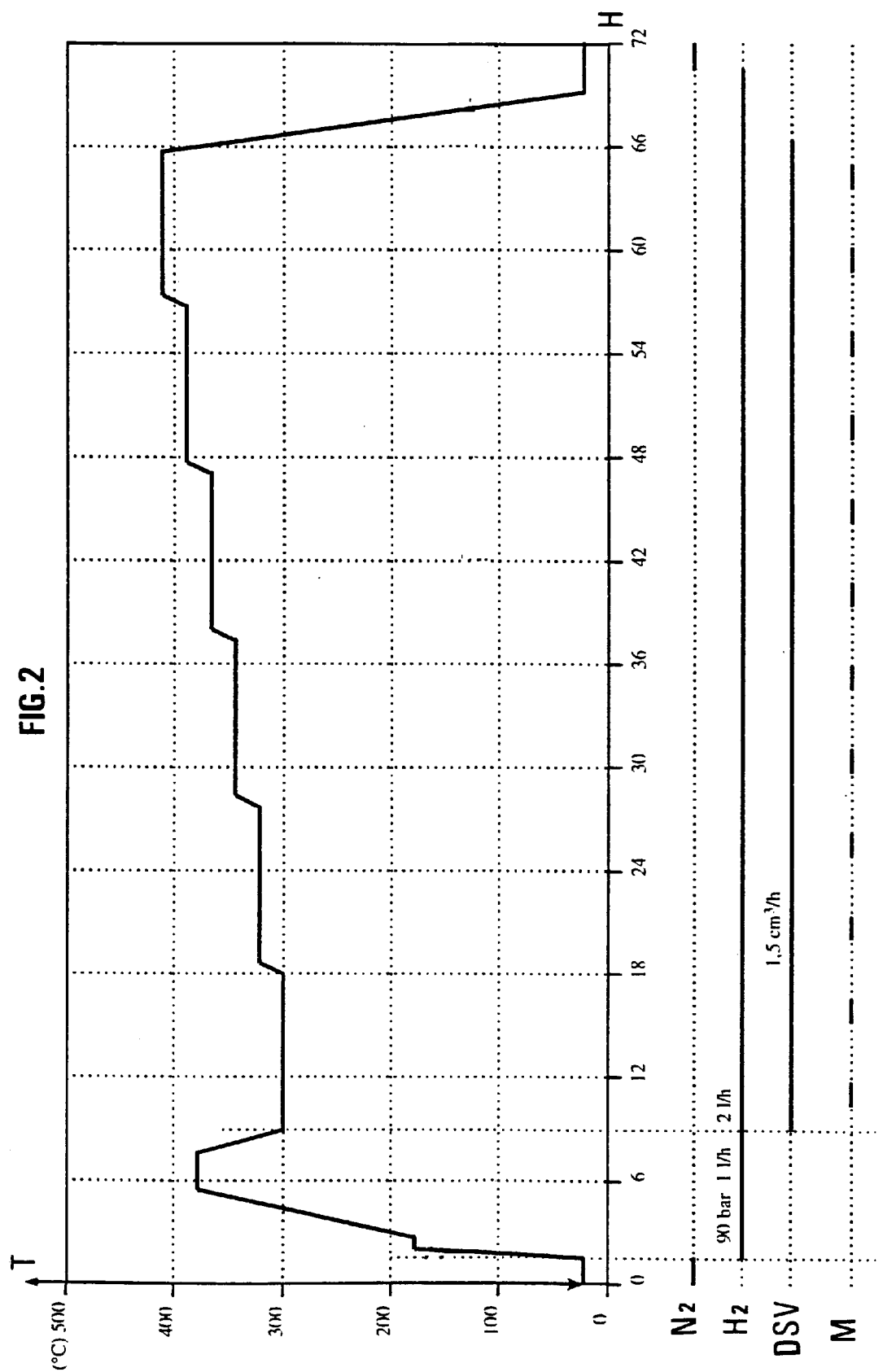
FIG. 2 shows an example of an operational diagram of a reactor.

This system allows to carry out complete cycles in parallel with reactors 3a, 3b, 3c, 3d. These cycles typically progress completely autonomously in several successive stages: pressure test of the assembly, flushing with an inert gas, activation of the catalyst if necessary, reaction with performance measurement and finally draining of the installation before it is stopped. An example of a cycle is shown in FIG. 2. The progress of the cycle is shown by the evolution of the temperature T of the reactor as a function of time H. The periods of injection of the reagents and of analysis are given as a function of time. A vacuum distillate is injected from 9H at a flow rate of 1.5 cm$^3$/h with 2 l/h hydrogen. Measuring stages M are carried out regularly, generally at a rate of at least one per temperature stage.

Figure 3:
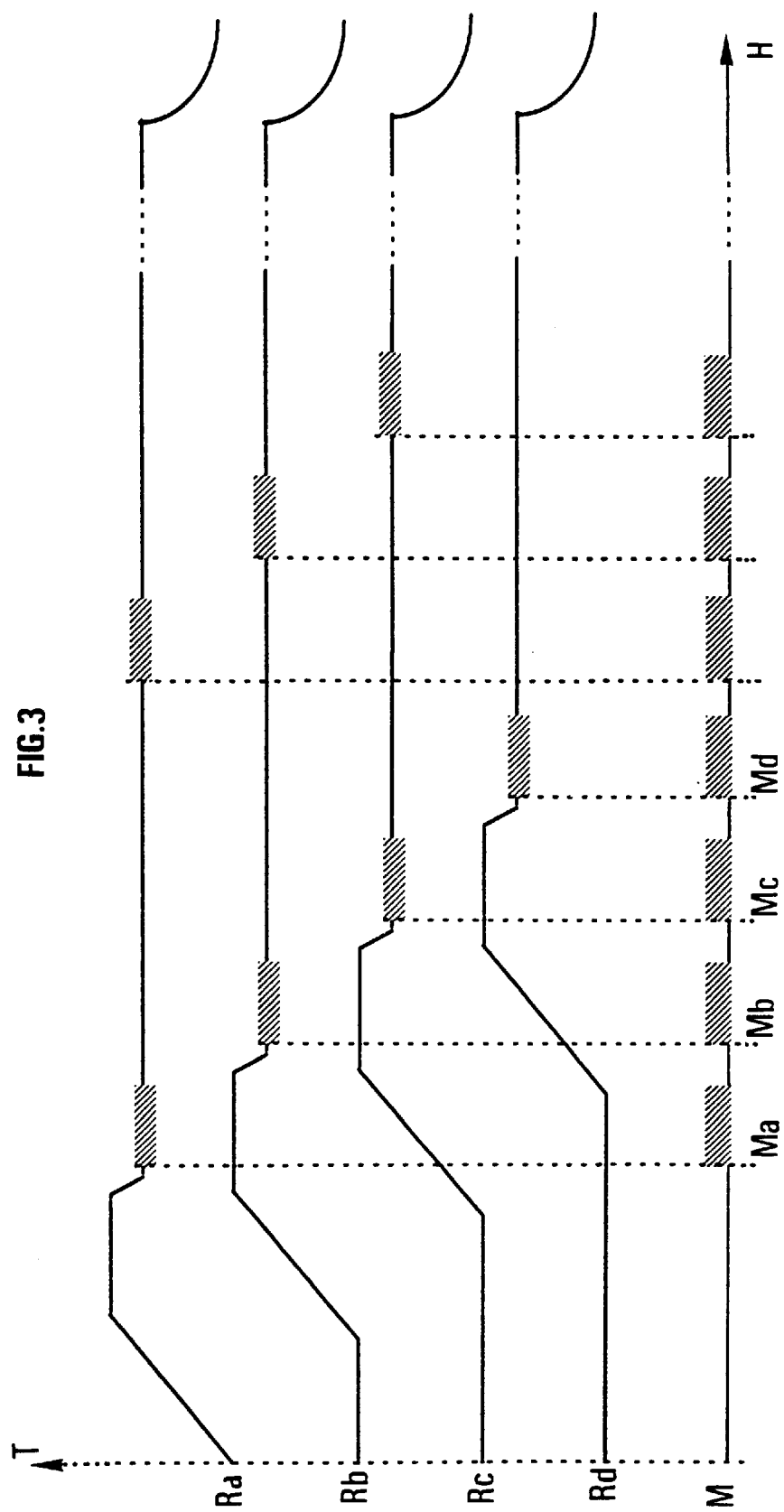
FIG. 3 illustrates the optimized operation of a device with four reactors.

The cycles of each reactor progress simultaneously. An example of combination of these cycles is given in FIG. 3. The effluents of each reactor Ra, Rb, Rc, Rd are analyzed in turn during stages Ma, Mb, Mc, Md. It can thus be noted that, despite the duration of each test cycle, it is possible to select one reactor after another to perform a measurement on an effluent, which allows to carry out four tests (in the present case) practically during the same time.

Example of Use

Four hydroconversion catalysts A, B, C and D contain Ni and Mo as the active metal phase and a zeolite of Y structure as the acid phase, but in different proportions. Fast evaluation of these four samples is sought in terms of activity and of global selectivity. A sample (1 g) of each one of these catalysts is therefore placed in one of the four reactors of the equipment according to the invention. A hydrotreated vacuum distillate having the following characteristics is used as the liquid reagent:

| | |
|---|---|
| density: | 0.871 g/cm$^3$ |
| pour point: | 45° C. |
| sulfur content: | 10 ppm by weight |
| nitrogen content: | 3 ppm by weight |
| viscosity at 50° C.: | 25 cSt |
| initial boiling point: | 340° C. |
| 5% point: | 379° C. |
| 10% point: | 397° C. |
| 30% point: | 429° C. |
| 50% point: | 446° C. |
| 70% point: | 462° C. |
| end boiling point: | 501° C. |

The operating conditions selected, identical for each reactor, are as follows:

| | |
|---|---|
| inlet pressure: | 9.0 10$^6$ Pa |
| flow rate of liquid reagent: | 0.800 g/h |
| flow rate of gaseous reagent H$_2$: | 0.80 l/h |
| temperature: | 5 successive stages (365, 375, 385, 395 and 410° C.). |

Prior to the reaction stage proper, an activation stage referred to as catalyst sulfuirization is carried out. This treatment consists in injecting into the reactor the sulfur-containing compound dimethyldisulfide dissolved (1.0% by weight) in normal heptane. The other conditions of this treatment are as follows:

| | |
|---|---|
| inlet pressure: | 6.0 10$^6$ Pa |
| flow rate of nC$_7$H$_{16}$/C$_2$H$_6$S$_2$: | 0.650 g/h |
| flow rate of gaseous reagant H$_2$: | 0.60 l/h |
| temperature: | 350° C. |
| duration: | 2 h. |

During the temperature stages of the reaction phase, the volumes of gas and the weights of liquid produced are measured during ½ h periods. Analysis of these gaseous and liquid fractions is carried out at the same time. All these operating conditions are programmed in the automaton. The corresponding cycles are close to the examples shown in FIGS. 2 and 3. During this time, there is no intervention by the operator.

The analysis results obtained are used to calculate the conversion of the vacuum distillate to products with a boiling point below 380° C. and the selectivity for production of cuts distilling between 150 and 380° C., which are the wanted products. The conversions and selectivity thus obtained are given in the table hereafter:

| | Catalyst | | A | B | C | D | |
|---|---|---|---|---|---|---|---|
| Temperature (° C.) | 365 | conversion | 60.0 | 54.4 | 28.0 | 52.3 | % by weight |
| | | selectivity | 69.0 | 72.1 | 82.0 | 63.4 | % |
| | 375 | conversion | 75.5 | 68.0 | 41.3 | 64.1 | % by weight |
| | | selectivity | 63.1 | 66.9 | 76.2 | 60.4 | % |
| | 385 | conversion | 92.1 | 82.4 | 51.6 | 77.9 | % by weight |
| | | selectivity | 54.2 | 60.0 | 75.0 | 54.3 | % |
| | 395 | conversion | 98.0 | 97.2 | 63.7 | 86.2 | % by weight |
| | | selectivity | 50.9 | 52.8 | 71.8 | 50.4 | % |

-continued

|     | Catalyst    | A    | B    | C    | D    |           |
|-----|-------------|------|------|------|------|-----------|
| 410 | conversion  | 99.3 | 98.9 | 82.2 | 97.5 | % by weight |
|     | selectivity | 48.6 | 52.0 | 64.1 | 46.2 | %         |

The activity of a catalyst is represented by the conversion level reached for a given temperature. The results clearly show great differences between these catalytic solids. Sample A is the most active whatever the temperature, whereas sample C is the most selective.

Applied to selection of catalytic solids, the equipment according to the invention thus allows fast, parallel and high-precision evaluation of several catalytic solids.

What is claimed is:

1. An equipment intended for measurement on an effluent resulting from a chemical reaction taking place in a reactor containing a catalyst, characterized in that it comprises in combination:
   - at least two reactors,
   - means for injecting at least one feedstock into each reactor,
   - means intended for gas and liquid phase separation downstream from each reactor,
   - distribution means for sending the gas phase coming from the separation means to first analysis and measuring means while the other gas phases coming from the other separators are discharged, wherein said distribution means comprise at least two inlet ways and two outlet ways, at least one closed-loop circuit divided into four sections by four controlled sealing elements, each of said four ways communicates with a single section so that the inlet ways are connected to two opposite sections and said outlet ways are connected to the other two sections,
   - second analysis and measuring means intended for the liquid phase coming from the separation means, and
   - means intended for automatic monitoring and control of the chemical reaction in said reactors, of the cycle of analysis and measurement performed on the gas phase and of the cycle of analysis and measurement performed on the liquid phase.

2. An equipment as claimed in claim 1, characterized in that it comprises four reactors.

3. An equipment as claimed in claim 2, wherein said distribution means comprise two closed-loop circuits and said outlet ways communicate together two by two so as to form a distribution device with four inlet ways and two outlet ways.

4. An equipment as claimed in claim 1, wherein the inside diameter of said reactors ranges between 0.5 and 3 cm, and their length ranges between 10 and 50 cm.

5. An equipment as claimed in claim 1, wherein the inside diameter of said reactors ranges between 1 and 2 cm, and their length ranges between 15 and 25 cm.

6. A method intended for analysis and measurement on an effluent produced by a chemical reaction taking place in a reactor containing a catalyst, wherein the following stages are carried out:
   - there are at least two reactors,
   - at least one feedstock is injected into each reactor,
   - the effluent produced by each reactor is separated into a liquid phase and a gas phase,
   - the gas phase is alternately sent to measuring and analysis means by distribution means that comprise at least two inlet ways and two outlet ways, at least one closed-loop circuit divided into four sections by four controlled sealing element, each of said four ways communicates with a singe section so that the inlet ways are connected to two opposite sections and said outlet ways are connected to the other two sections,
   - analyses and measurements are carried out on the liquid phase,
   - the progress of the reaction, analysis and measurement cycles performed on each phase is controlled with the aid of automatic monitoring and control means.

7. A method as claimed in claim 6, wherein the material balances of each reaction are determined.

8. A method as claimed in claim 6, wherein the temperature and the pressure of the gaseous effluents are controlled between the outlet of the separation means and the measuring and analysis means, including the distribution means, so that said effluent remains gaseous.

9. Application of the method as claimed in claim 6 in order to compare the characteristics of different catalysts used in each reactor.

10. Application of the method as claimed in claim 6 in order to determine the optimum conditions of use of a catalyst for a determined reaction by varying the parameters of said reaction in each reactor.

* * * * *